(12) United States Patent
Thaveeprungsriporn et al.

(10) Patent No.: US 11,452,458 B2
(45) Date of Patent: Sep. 27, 2022

(54) METHOD OF DERIVING SYSTOLIC BLOOD PRESSURE AND/OR DIASTOLIC BLOOD PRESSURE OF A SUBJECT

(71) Applicant: Nitto Denko Corporation, Osaka (JP)

(72) Inventors: Visit Thaveeprungsriporn, Singapore (SG); Somchai Baotong, Singapore (SG); Srisuda Aphaipanan, Singapore (SG); Amornsri Khitwongwattana, Singapore (SG)

(73) Assignee: Nitto Denko Corporation

( * ) Notice: Subject to any disclaimer, the term of this patent is extended or adjusted under 35 U.S.C. 154(b) by 1026 days.

(21) Appl. No.: 16/088,685

(22) PCT Filed: Apr. 1, 2016

(86) PCT No.: PCT/SG2016/050165
§ 371 (c)(1),
(2) Date: Sep. 26, 2018

(87) PCT Pub. No.: WO2017/171632
PCT Pub. Date: Oct. 5, 2017

(65) Prior Publication Data
US 2019/0110702 A1    Apr. 18, 2019

(51) Int. Cl.
*A61B 5/02*    (2006.01)
*A61B 5/024*   (2006.01)
(Continued)

(52) U.S. Cl.
CPC ...... *A61B 5/02416* (2013.01); *A61B 5/02108* (2013.01); *A61B 5/7239* (2013.01);
(Continued)

(58) Field of Classification Search
CPC ............ A61B 5/02416; A61B 5/02108; A61B 5/7239; A61B 5/7278; A61B 5/02141;
(Continued)

(56) References Cited

U.S. PATENT DOCUMENTS

2007/0232939 A1  10/2007  Forstner
2010/0324389 A1* 12/2010  Moon ............... A61B 5/681
                                              600/324
(Continued)

FOREIGN PATENT DOCUMENTS

EP    0536782 A1    4/1993
EP    3033991 A1    6/2016
(Continued)

OTHER PUBLICATIONS

English-language machine translation of the description of WO-2015098977-A1 (Year: 2021).*
(Continued)

*Primary Examiner* — Andrey Shostak
(74) *Attorney, Agent, or Firm* — Lerner, David, Littenberg, Krumholz & Mentlik, LLP

(57) ABSTRACT

A method (200) of deriving systolic blood pressure and/or diastolic blood pressure of a subject is disclosed. The method comprises: (i) receiving (202) data related to at least one cardiac cycle of a bio-signal from the subject; (ii) calculating (208) a rise time and a fall time of the at least one cardiac cycle based on the received data; (iii) calculating (208) a parameter derived from a function of the rise time and fail time; and (iv) determining (210) the systolic blood pressure and/or diastolic blood pressure of the subject based on the calculated parameter. A related apparatus is also disclosed.

16 Claims, 10 Drawing Sheets

(51) Int. Cl.
  *A61B 5/021* (2006.01)
  *A61B 5/00* (2006.01)
  *A61B 5/022* (2006.01)
  *A61B 5/0225* (2006.01)
  *A61B 5/1455* (2006.01)

(52) U.S. Cl.
  CPC .......... *A61B 5/7278* (2013.01); *A61B 5/0225* (2013.01); *A61B 5/02141* (2013.01); *A61B 5/02225* (2013.01); *A61B 5/1455* (2013.01)

(58) Field of Classification Search
  CPC .. A61B 5/02225; A61B 5/0225; A61B 5/1455
  See application file for complete search history.

(56) References Cited

U.S. PATENT DOCUMENTS

| | | | |
|---|---|---|---|
| 2013/0023778 A1 | 1/2013 | Sawanoi et al. | |
| 2015/0245777 A1* | 9/2015 | Della Torre | A61B 5/11 600/301 |
| 2016/0038045 A1* | 2/2016 | Shapiro | A61B 5/721 600/479 |
| 2016/0302735 A1* | 10/2016 | Noguchi | A61B 5/746 |

FOREIGN PATENT DOCUMENTS

| | | | |
|---|---|---|---|
| JP | H08229012 A | 9/1996 | |
| JP | 2011229736 A | 11/2011 | |
| WO | 2000022983 A1 | 4/2000 | |
| WO | 2012140537 A1 | 10/2012 | |
| WO | 2015098977 A1 | 7/2015 | |
| WO | WO-2015098977 A1 * | 7/2015 | ............. A61B 5/746 |

OTHER PUBLICATIONS

Supplemental European Search Report for EP16897248 dated Oct. 25, 2019.
International Search Report for PCT/SG2016/050165, dated Jun. 7, 2016.
Millasseau, et al., "Determination of Age-Related Increases in Large Artery Stiffness by Digital Pulse Countour Analysis", Clinical Science, vol. 103, No. 4, Oct. 2002, pp. 371-377.

* cited by examiner

800

|  | Mean difference vs. conventional device (± standard deviation) |
|---|---|
| Systolic blood pressure (mmHg) | 0.89 ± 6.59 |
| Diastolic blood pressure (mmHg) | 1.19 ± 3.59 |

METHOD OF DERIVING SYSTOLIC BLOOD PRESSURE AND/OR DIASTOLIC BLOOD PRESSURE OF A SUBJECT

CROSS REFERENCE TO RELATED APPLICATIONS

The present application is a national phase entry under 35 U.S.C. § 371 of International Application No. PCT/SG2016/050165 filed on Apr. 1, 2016, the disclosure of which is hereby incorporated herein by reference.

FIELD

The present invention relates to a method and apparatus for deriving systolic blood pressure and/or diastolic blood pressure of a subject.

BACKGROUND

In many medical institutions (e.g. hospitals and nursing homes), the quality of patient care afforded is often jeopardized by the increasingly hectic working environment. This is due to the ever increasing work load imposed on medical care personnel as monitoring of multiple physiological parameters (e.g. heart rate, respiratory rate, blood oxygen saturation, arterial blood pressure and/or temperature) of each patient has already become a modern clinical routine. Frequently, this is worsened by the constantly increasing patients-to-staff ratio due to worker shortage in the field of health care. As the medical care personnel make their rounds to each patient, they will have to measure various physiological parameters using a variety of measurement devices, and the patients face unnecessary stress from having to be hooked up to multiple measurement devices. For example, a stethoscope is used to measure heart rate, a finger oximeter for blood oxygen level, an inflatable cuff for blood pressure, and a thermometer for body temperature. Additional stressors may also come in the form of discomfort, while the measurement devices are attached to the patient. For example, compression pressure exerted on the patient's arm when the blood pressure cuff is inflated may cause slight discomfort to the patient. Once the measurement is completed, a common practice is to manually record the results before inputting the recorded data into a centralized database from a central station. It will thus be appreciated that handling such huge amount of data using manual procedures is both fairly time consuming and error-prone.

Similar problems exist in patient self-care environments. Patients have to face unnecessary stress and hassle from utilizing multiple devices for measurements and recording results without any real time prognosis being provided to them.

Further, it can be a costly affair for these patients as they are required to acquire multiple medical devices, which are often sold at high prices.

Thus, it is desirable for a single "all-in-one" device that is capable of concurrently capturing multiple physiological parameters within a single measurement and hence facilitating the error-free measurement procedures, providing comfort and reducing stress induced on patients. The device should also preferably include functions of automatic patient identification, automated transmission of data to a centralized database for storage and future access, automated computation and generation of result trends and alerts, and provision of means for real time communication with specialized medical personnel for immediate diagnosis. Only then with such a device can the overall quality of the patient care provided in both environments be improved.

Separately, it is to be appreciated that arterial blood pressure measurements provide valuable information about a patient's cardiovascular system. A normal cardiovascular system is characterized by sufficient blood flow to all parts of a patient's body, without producing prolonged strain on the physical capabilities of various organs through which blood flows. In an abnormal cardiovascular system, blood pressure may be too high or too low, with each abnormality having attendant consequences for various body parts. The resultant prolonged strain may lead to heart, liver and/or kidney diseases, and other complications. Hence, the importance of arterial blood pressure has spurred the development of numerous methods for determining it. One existing solution is to adapt the method of blood pressure measurement to use a pulse oximeter instead. With that, at least both the blood oxygen saturation and blood pressure may be determined in a single measurement.

Presently, the auscultation and oscillometric techniques are the most widely used techniques for measuring blood pressure. Specifically, blood pressure is determined based on the relationship between arterial pulsations and an external applied pressure. Hence an air pump with an inflatable cuff (forming a system) are required, giving rise to two main disadvantages of cuff-based pressure monitoring systems. Firstly, the system may be too bulky and not conveniently portable for continuous blood pressure monitoring. Secondly, use of inflated cuff during measurement may cause discomfort to the patient and/or vasoconstriction, thereby in turn influence blood pressure readings to be inaccurate.

Then, more advanced blood pressure monitoring systems that provide cuff-less measurement are typically based on photoplethysmography (PPG) and/or electrocardiogram (ECG) signals. Features such as pulse transit time (PTT) and pulse arrival time (PAT) are extracted from the said signals to determine the blood pressure. For measurement, multiple sensing devices are required to be attached to more than one location on the patient's body, also creating discomfort and hassle during usage. It should be mentioned that those systems are also susceptible to measurement inaccuracies due to external factors such as placement sensitivity, calibration difficulties and motion sensitivity.

There are also other known methods to perform cuff-less and single site measurement. However, those methods are unable to achieve optimal measurement results for older subjects, which is an inherent problem largely arising from usage of non-prominent waveform features such as the dicrotic notch and/or diastolic peak for calculation. Briefly, the waveform at any point along the arteries is a summation of the incident and reflected waves: the incident travelling wave from heart to periphery, and the reflected wave travelling from the periphery site of wave reflection to the heart. In younger subjects, where arteries are distensible, the pulse wave velocity is relatively low. But for older subjects, their arteries are however stiffer due to age and so a velocity of the pulse wave velocity is high (i.e. the reflected wave returns faster), thus causing the interval between the systolic and diastolic peaks to decrease. From summation of the waves, the dicrotic notch and the diastolic peak of the pulse wave thus become less visually distinguishable.

This effect is evidently seen from FIG. 9 (i.e. referenced from Millasseau et al., Clinical Science (2002) 103, 371-377). With base reference to a 29 years old test subject (i.e. see systolic peak 902, diastolic peak 914 and dicrotic notch 908), it may be observed from FIG. 9 that in older subjects the dicrotic notch (i.e. see features labelled as 910 and 912)

as well as diastolic peak (i.e. see features labelled as 916 and 918) indeed become much less visually distinguishable with increasing age. As the precise locations of these waveform features are difficult to determine, this results in a significant degree of error when performing calculations that are utilizing such features.

One object of the present invention is therefore to address at least one of the problems of the prior art and/or to provide a choice that is useful in the art.

SUMMARY

According to a $1^{st}$ aspect of the invention, there is provided a method of deriving systolic blood pressure and/or diastolic blood pressure of a subject, the method comprises: (i) receiving data related to at least one cardiac cycle of a bio-signal from the subject; (ii) calculating a rise time and a fall time of the at least one cardiac cycle based on the received data; (iii) calculating a parameter derived from a function of the rise time and fall time; and (iv) determining the systolic blood pressure and/or diastolic blood pressure of the subject based on the calculated parameter.

Beneficially, the proposed method enables an accurate blood pressure value to be measurable using a single optical sensor device, without needing an inflatable cuff, and further without requiring identification of the dicrotic notch and the diastolic peak of an arterial waveform for analysis.

Preferably, the rise time may be calculated between a start of the at least one cardiac cycle to a systolic peak of the at least one cardiac cycle.

Preferably, the fall time may be calculated from the systolic peak of the at least one cardiac cycle to an end of the at least one cardiac cycle.

Preferably, the rise time may be calculated between 10% and 90% of a systolic peak of the at least one cardiac cycle.

Preferably, the bio-signal may include an arterial photoplethysmography (PPG) signal.

Preferably, the method may further comprise processing the PPG signal to digitally filter noise signals in the PPG signal.

Preferably, digitally filtering the noise signals in the PPG signal may include using a band pass filter configured to only permit signals having a frequency of between 0.5 Hz to 8.0 Hz to pass through the band pass filter.

Preferably, the data may relate to a plurality of cardiac cycles, and the method then includes calculating the rise time and the fall time of each of the cardiac cycles; calculating parameters respectively derived from a function of the rise time and fall time of each of the cardiac cycles; and calculating an average parameter based on the respectively calculated parameters as the parameter in step (iii).

Preferably, the cardiac cycles may be arranged consecutively.

Preferably, calculating the parameter derived from the function of the rise time and fall time may include calculating the parameter according to the equation: $f=(T_r)^x \times (T_f)^y$, where $f$ is the parameter; $T_r$ is the rise time; $T_f$ is the fall time; and x and y are predetermined constants selected from a range of between −3 to 3, and exclusive of 0.

Preferably, the data may include time intervals of the at least one cardiac cycle relating to a systolic peak, start time and end time of the at least one cardiac cycle.

Preferably, the method may further comprises determining the systolic peak, start time and end time by a first electronic device and transmitting the determined systolic peak, start time and end time to a second electronic device for calculating the rise time and fall time.

Preferably, determining the systolic blood pressure may include determining the systolic blood pressure according to the equation: $SBP=c_1 \times f+c_2+c_3$, where SBP is the systolic blood pressure; $f$ is the parameter; and $c_1$, $c_2$, and $c_3$ are predetermined constants.

Preferably, determining the diastolic blood pressure may include determining the diastolic blood pressure according to the equation: $DBP=\sqrt{2 \times eQM^2 - SBP^2}+c_6$, where DBP is the diastolic blood pressure; eQM is an estimated quadratic mean; SBP is the systolic blood pressure; and $c_6$ is a predetermined constant.

Preferably, the estimated quadratic mean may be determined according to the equation: $eQM=c_4 \times SBP+c_5$, where eQM is an estimated quadratic mean; SBP is the systolic blood pressure; and $c_4$, and $c_5$ are predetermined constants.

According to a $2^{nd}$ aspect of the invention, there is provided a computer program for deriving systolic blood pressure and/or diastolic blood pressure of a subject, the computer program downloadable to an electronic device and includes a set of instructions, when executed, is arranged to control a processor of the electronic device to: (i) receive data related to at least one cardiac cycle of a bio-signal from the subject; (ii) calculate a rise time and a fall time of the at least one cardiac cycle based on the received data; (iii) calculate a parameter derived from a function of the rise time and fall time; and (iv) determine the systolic blood pressure and/or diastolic blood pressure of the subject based on the calculated parameter.

According to a $3^{rd}$ aspect of the invention, there is provided a computer program stored in a memory of an electronic device, the computer program having a set of instructions, when executed, is arranged to control a processor of the electronic device to: (i) receive data related to at least one cardiac cycle of a bio-signal from the subject; (ii) calculate a rise time and a fall time of the at least one cardiac cycle based on the received data; (iii) calculate a parameter derived from a function of the rise time and fall time; and (iv) determine the systolic blood pressure and/or diastolic blood pressure of the subject based on the calculated parameter.

Preferably, the computer program may be downloadable over the internet.

According to a $4^{th}$ aspect of the invention, there is provided an apparatus for deriving systolic blood pressure and/or diastolic blood pressure of a subject, the apparatus comprising: (i) a receiver for receiving data related to at least one cardiac cycle of a bio-signal from the subject; and (ii) a processor for: (a) calculating a rise time and a fall time of the at least one cardiac cycle based on the received data; (b) calculating a parameter derived from a function of the rise time and fall time; and (c) determining the systolic blood pressure and/or diastolic blood pressure of the subject based on the calculated parameter.

An advantage of the proposed apparatus is being able to determine the systolic blood pressure and/or diastolic blood pressure (of the subject), without requiring an inflatable cuff.

Preferably, the apparatus may be in the form of an electronic device.

Preferably, the electronic device may be a telecommunications device or an optical measurement device.

Preferably, the apparatus may include an optical measurement device and a telecommunications device having the receiver; and wherein the optical measurement device includes a signal sensing device for obtaining the bio-signal from the subject, and a data processing module for determining data relating to the bio-signal, wherein the receiver of the telecommunications device is arranged to receive the determined data of the bio-signal.

It should be apparent that features relating to one aspect of the invention may also be applicable to the other aspects of the invention.

These and other aspects of the invention will be apparent from and elucidated with reference to the embodiments described hereinafter.

BRIEF DESCRIPTION OF THE DRAWINGS

Embodiments of the invention are disclosed hereinafter with reference to the accompanying drawings, in which.

DETAILED DESCRIPTION OF PREFERRED EMBODIMENTS

Figure 1:
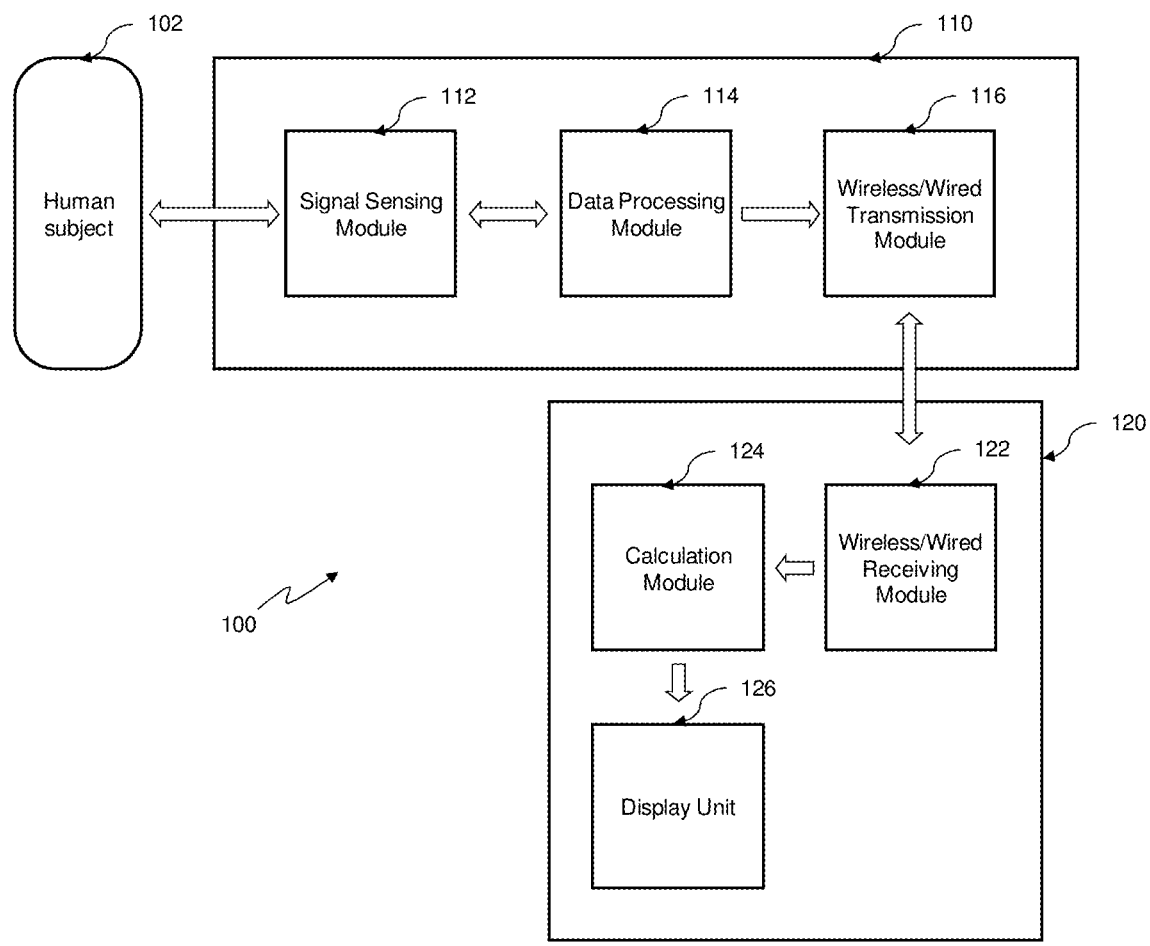
FIG. 1 is a schematic block diagram of an apparatus for measuring the blood pressure of a subject, based on a first embodiment of the invention.

FIG. 1 is a schematic block diagram of an apparatus 100 for measuring blood pressure of a (human or animal) subject 102 according to a first embodiment. In particular, measuring blood pressure herein refers to deriving systolic blood pressure and/or diastolic blood pressure of the subject 102. The apparatus 100 includes an optical measurement device 110 comprising a signal sensing module 112 for obtaining a bio-signal from the said subject 102. The optical measurement device 110 further includes a data processing module 114 (e.g. a processor) which is arranged to receive and process the bio-signal from the signal sensing module 112, and a wireless/wired transmission module 116 for transmitting data processed from the bio-signal. It is to be appreciated that the optical measurement device 110 is preferably arranged to be conveniently portable, for example in a palm-sized form factor.

The transmission module 116 of the optical measurement device 110 is arranged to communicate wirelessly/non-wirelessly with a telecommunications device 120 (e.g. a mobile phone or other portable electronic devices). The telecommunications device 120, which is part of the apparatus 100, includes a receiving module 122 for receiving signals from the optical measurement device 110, a calculation module 124 (e.g. a processor) and a display unit 126 for displaying a result or information to a user of the apparatus 100. The receiving module 122 is configured to receive the signals from the optical measurement device 110 wired/wirelessly, depending on the corresponding setup of the transmission module 116 of the optical measurement device 110.

Figure 2:
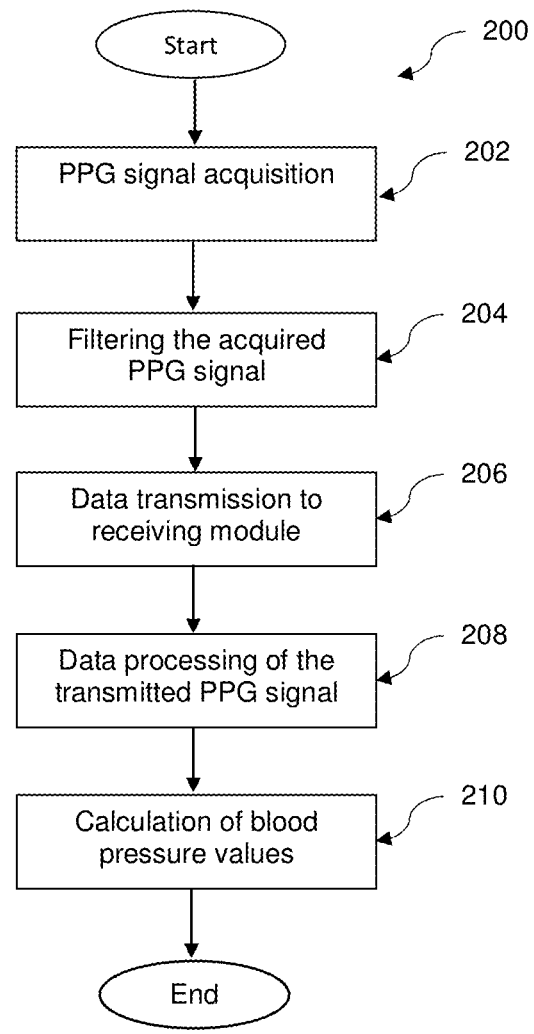
FIG. 2 is a flow diagram of a method, performed by the apparatus of FIG. 1, for deriving systolic blood pressure and/or diastolic blood pressure of the subject.
Figure 3:
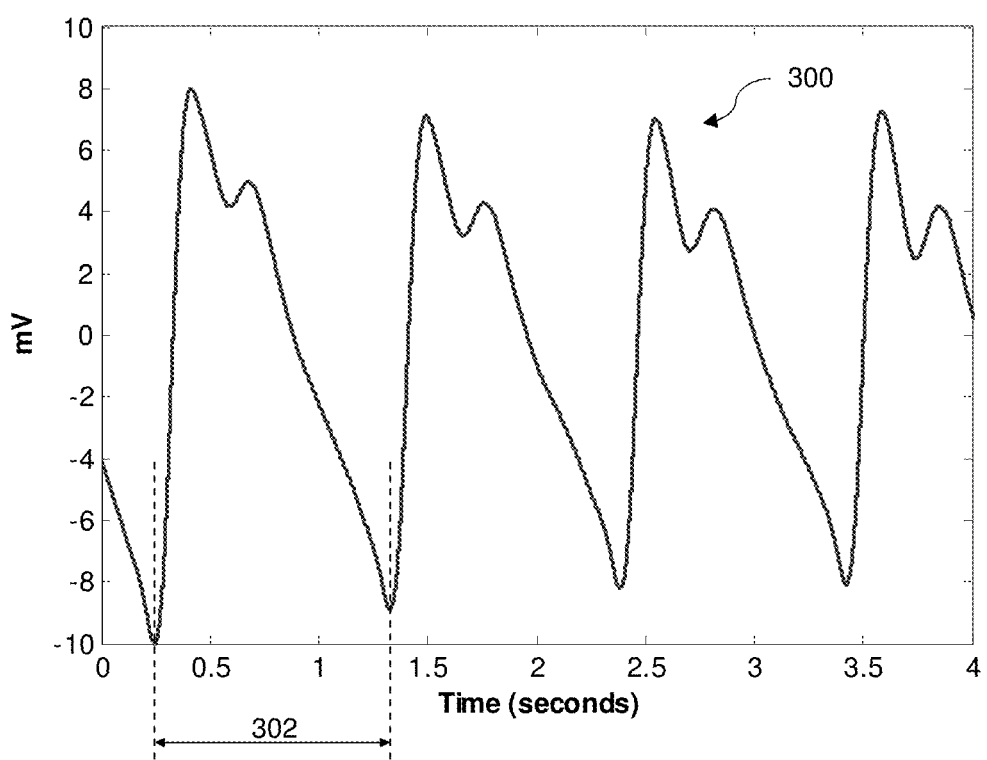
FIG. 3 is a diagram of a PPG signal having at least a cardiac cycle.

FIG. 2 shows a method 200 for deriving systolic blood pressure and/or diastolic blood pressure of the subject 102, whereby said method 200 is performed by the apparatus 100 of FIG. 1. A brief overview of steps 202-210 of the method 200 is first described, with detailed description of each step to follow further below. At step 202, signal acquisition is performed to obtain a bio-signal from the subject 102, and at next step 204, the acquired bio-signal is filtered to provide a processed signal. In this embodiment, the bio-signal is an arterial PPG waveform signal 300 comprising at least one cardiac cycle 302, for example as depicted in FIG. 3. But in other variant embodiments, it is however to be appreciated that a plurality of cardiac cycles 302-306 (as depicted in FIG. 3) may also be utilised to provide better accuracy of results, and the plurality of cardiac cycles 302-306 are arranged consecutively together. At following step 206, the processed signal (from step 204) is transmitted to the calculation module 124 of the telecommunications device 120, i.e. transmission is made from the wired/wireless transmission module 116 (of the optical measurement device 110) to the receiving module 122 (of the telecommunications device 120). Then at step 208, the received processed signal is data processed by the calculation module 124 of the telecommunications device 120 to obtain a rise time and a fall time of the least one cardiac cycle 302. Finally, at step 210, the systolic blood pressure and/or diastolic blood pressure of the subject 102 are calculated based on a parameter derived from a function of the rise time and fall time, i.e. see equation (1). It is to be appreciated that steps 206, 208 may be performed by the apparatus 100 sequentially or in parallel, depending on a specific desired implementation.

The above mentioned steps 202-210 of the method in FIG. 2 are respectively described in greater detail set out below.

1. Step 202 of the Method

At step 202, signal acquisition is performed by the optical measurement device 110 using the signal sensing module 112 to obtain a bio-signal from the subject 102 and as mentioned, the bio-signal is the arterial PPG waveform signal 300 (hereafter "PPG signal" for brevity) shown in FIG. 3. It is to be appreciated that the PPG signal 300 includes time intervals relating to a systolic peak, a start time and an end time of the at least one cardiac cycle 302. The PPG signal 300 may be acquired from any peripheral sites of a subject's body such as wrist and/or finger. It has been empirically determined that an accuracy suitable for calculating the subject's blood pressure may for example, but without being limiting, be achieved by configuring the signal sensing module 112 to employ a measurement window of at least 30 seconds to obtain the subject's bio-signal.

2. Steps 204 and 206 of the Method

Figure 4:
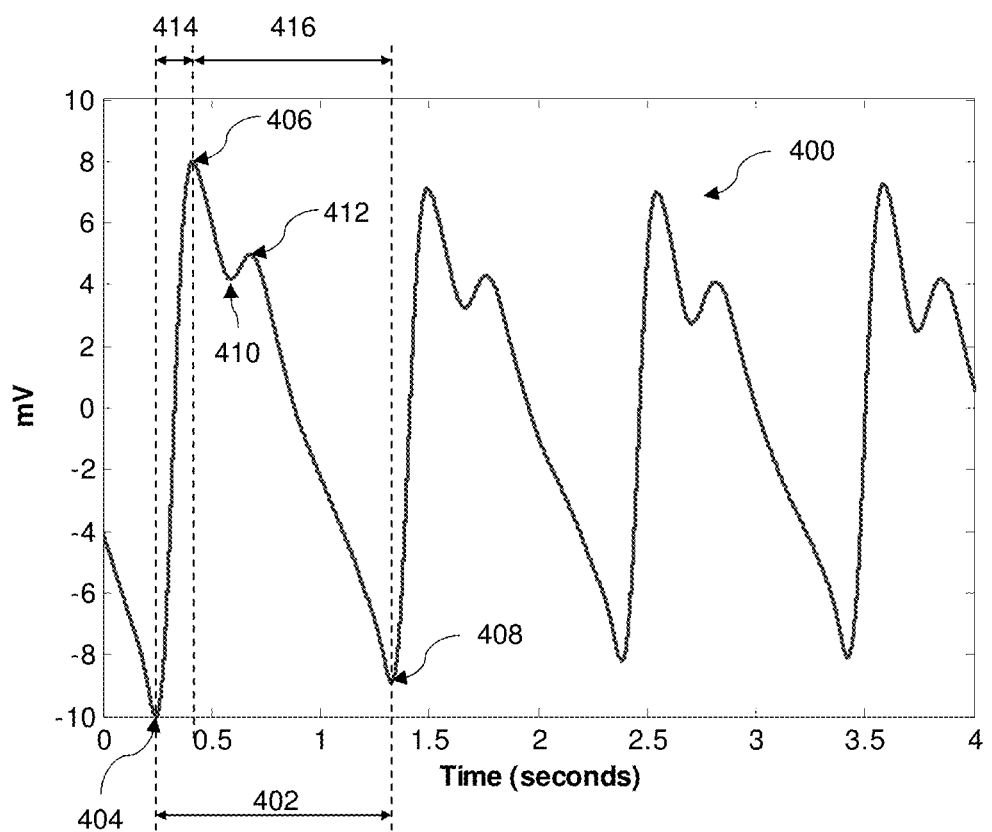
FIG. 4 is a diagram showing a rise time and a fall time of a cardiac cycle included in a PPG signal.

The acquired PPG signal 300 is then passed to the data processing module 114 for processing at step 204. The data processing module 114 may include a predefined digital band pass filter (not shown), or a low pass filter for digitally filtering any noise and signal artifacts present in the acquired PPG signal 300 to beneficially provide a filtered PPG signal (not shown). In this case, reference to the filtered PPG signal will instead be made to FIG. 4 as the filtered PPG signal 400, which includes a (filtered) cardiac cycle 402 of the at least one cardiac cycle 302.

Following from step 206, the filtered PPG signal 400 is transmitted to the calculation module 124 of the telecommunications device 120 to be further processed. It is to be appreciated that the filtered PPG signal 400 received by the telecommunications device 120 may be further processed with band pass filtering. In this respect, a digital band pass filter may be provided at the calculation module 124, and configured to only permit signals in the frequency range from 0.5 Hz to 8.0 Hz to pass through.

3. Step 208 of the Method

Detecting Peak and Valley

At step 208, (with reference to FIG. 4) the calculation module 124 is configured to detect a first valley position 404, a start point 404 (which coincides with the first valley position 404), a peak position, a systolic peak 406 and a second valley position 408, an end point 408 (which coincides with the second valley position 408) of the cardiac cycle 402. To elaborate, the time intervals representing the start point 404, end point 408 and the systolic peak 406 of the cardiac cycle 402 are obtained by the calculation module 124 to determine data relating to at least one cardiac cycle of the filtered PPG signal 400. It should be appreciated that the filtered PPG signal 400 also includes a dicrotic notch 410 and a diastolic peak 412, but this embodiment however does not make use of the dicrotic notch 410/diastolic peak 412 to determine the blood pressure (but is not to be construed as limiting in any way).

Calculating Rise and Fall Time

The calculation module 124 is configured to calculate a rise time based on the start point 404 and the systolic peak 406 of the cardiac cycle 402. Mathematically, referring to FIG. 4, the rise time for the cardiac cycle 402 is thus the time interval (denoted by reference numeral 414) measured between the start point 404 and the systolic peak 406. More preferably, it is to be appreciated that the rise time is calculated between 10% and 90% of a systolic peak of the at least one cardiac cycle. Further, the calculation module 124 also obtains a fall time of cardiac cycle 402. Mathematically, the fall time is the time interval (denoted by reference numeral 416) measured between the systolic peak 406 and the end point 408.

Calculating a Parameter Derived from a Function of Rise Time and Fall Time

Next a parameter to be derived from a function of the rise time and fall time, as obtained previously, is calculated according to equation (1):

$$f = (T_r)^X \times (T_f)^Y \quad (1)$$

in which $f$ is the parameter, $T_r$ is the rise time, $T_f$ is the fall time, and x and y are predetermined constants respectively selected from a range of between −3 to 3 (i.e. −3≤x, y≤3, where x and y are not equal to zero). The value of x is preferably in range of 0 to 3 (i.e. 0<x≤3), more preferably in range of 1 to 3 (i.e. 1≤x≤3), and more preferably in range of 1 to 2 (i.e. 1≤x≤2). The value of y is preferably in range of −3 to 0 (i.e. −3≤y<0), more preferably in range of −3 to −1 (i.e. −3≤y≤−1), and more preferably in range of −2 to −1 (i.e. −1≤y≤−2). It is to be appreciated that in this embodiment, the respective values of x and y are 1 and −1. So this means equation (1) takes the simplified form set out in equation (2) below:

$$f = \frac{T_r}{T_f} \quad (2)$$

With reference to equation (2), in the event that the filtered PPG signal 400 includes a plurality of (filtered) cardiac cycles, an average ratio corresponding to dividing the sum of all ratios (of rise time over fall time) over the total number of cardiac cycles.

Moreover, additional mathematical operations may be performed to improve accuracy of the eventually calculated blood pressure values. For example, the calculation module 124 may also be configured to further perform a further outlier filtering process to identify and remove outlier percentage of rise time over fall time that are affected by any noise and signal artifacts. Statistical operations such as calculating the mean, moving average, standard deviation or combinations thereof, may be used by the calculation module 124 to define outlier values. In one exemplary but non-limiting example, value of percentage of rise time over fall time that are not determined to be within 50% of data at the centre, or one standard deviation (sigma) derived from all values of percentage of rise time over fall time in the measurement window are classified as outliers and will be removed from subsequent calculations. Accordingly, an average percentage of rise time over fall time is calculated based on all the non-outlier values based on equation (3):

Average % of rise time/fall time=Sum of all (non-outlier % rise time/fall time)/No. of (non-outlier % rise time/fall time) (3)

For good order, it is to be noted that equation (3) is used only in the event that the filtered PPG signal 400 includes a plurality of cardiac cycles, and is also optional under such circumstances.

4. Step 210 of the Method

Figure 5:
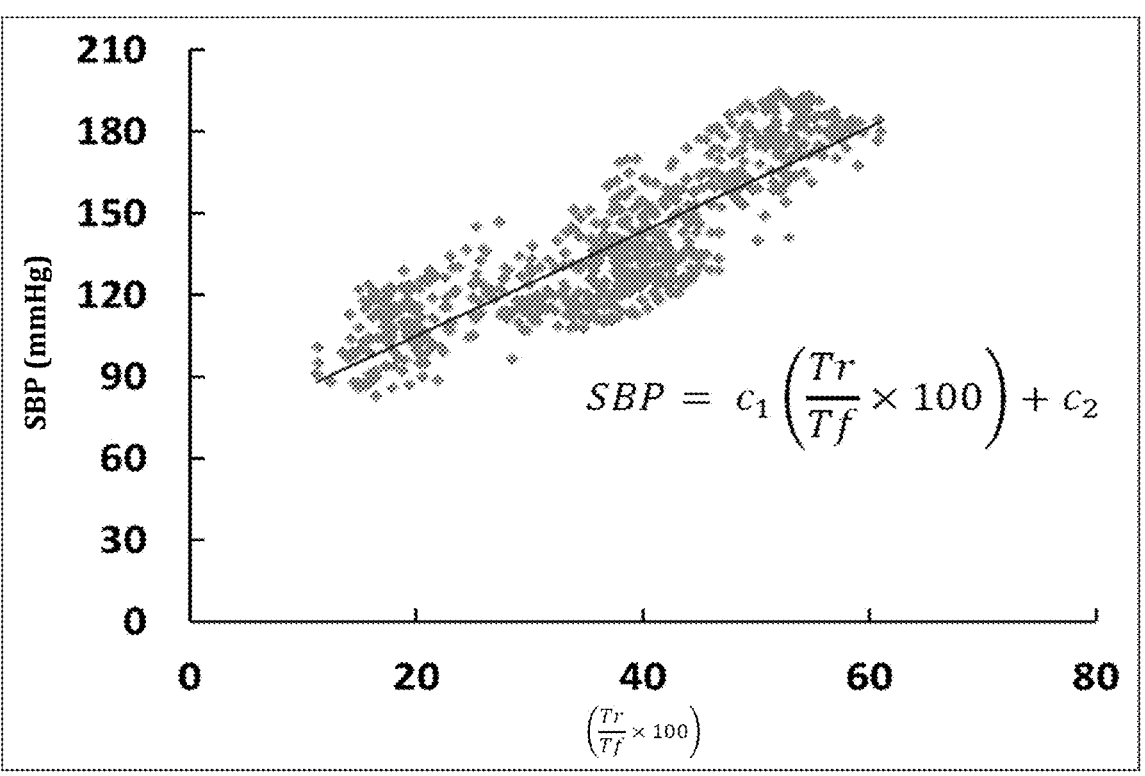
FIG. 5 is a diagram depicting the correlation between systolic blood pressure values versus measured average of percentage of rise time over fall time.
Figure 7:
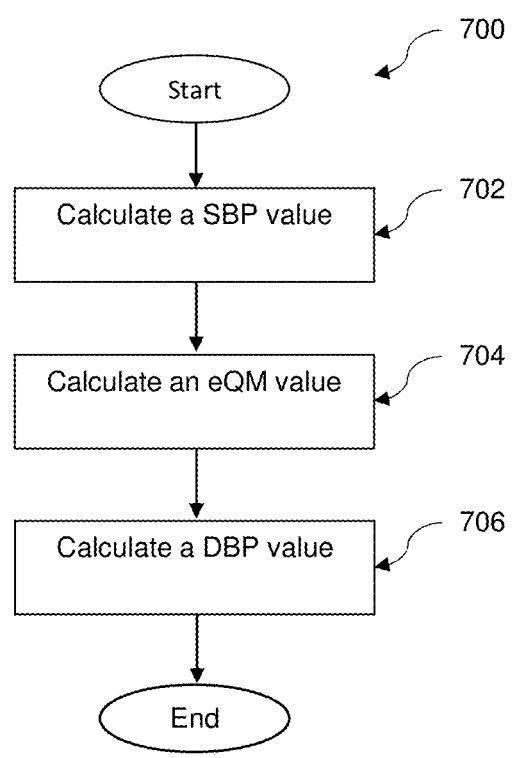
FIG. 7 is a flow diagram of step 210 of the method of FIG. 2 for calculating the systolic blood pressure and/or diastolic blood pressure of the subject.

At step 210, the calculation module 124 (of the telecommunications device 120) calculates the systolic blood pressure and/or diastolic blood pressure of the subject 102 using the parameter derived from equation (1), and more specifically in this embodiment, equation (2). In particular, performance of the step 210 is detailed in a method 700 of FIG. 7. At step 702, the calculation module 124 calculates a systolic blood pressure (SBP) of the subject 102 according to equation (4):

$$SBP = c_1 \times f + c_2 + c_3 \quad (4)$$

in which SBP is the systolic blood pressure; $f$ is the parameter; and $c_1$, $c_2$, and $c_3$ are predetermined constants. It is to be appreciated that the constants, $c_1$, and $c_2$, may be determined based on correlation of actual clinical data as shown in FIG. 5, which is a diagram 500 depicting the correlation between systolic blood pressure values versus measured average of percentage of rise time over fall time.

Once the constants, $c_1$, and $c_2$ are determined, equation (4) is input into the calculation module 124 for future calculations of arterial pressure, without beneficially need for further user-specific calibration procedures (relating to SBP measurements for the same user for which $c_1$, and $c_2$ were determined).

Figure 6:
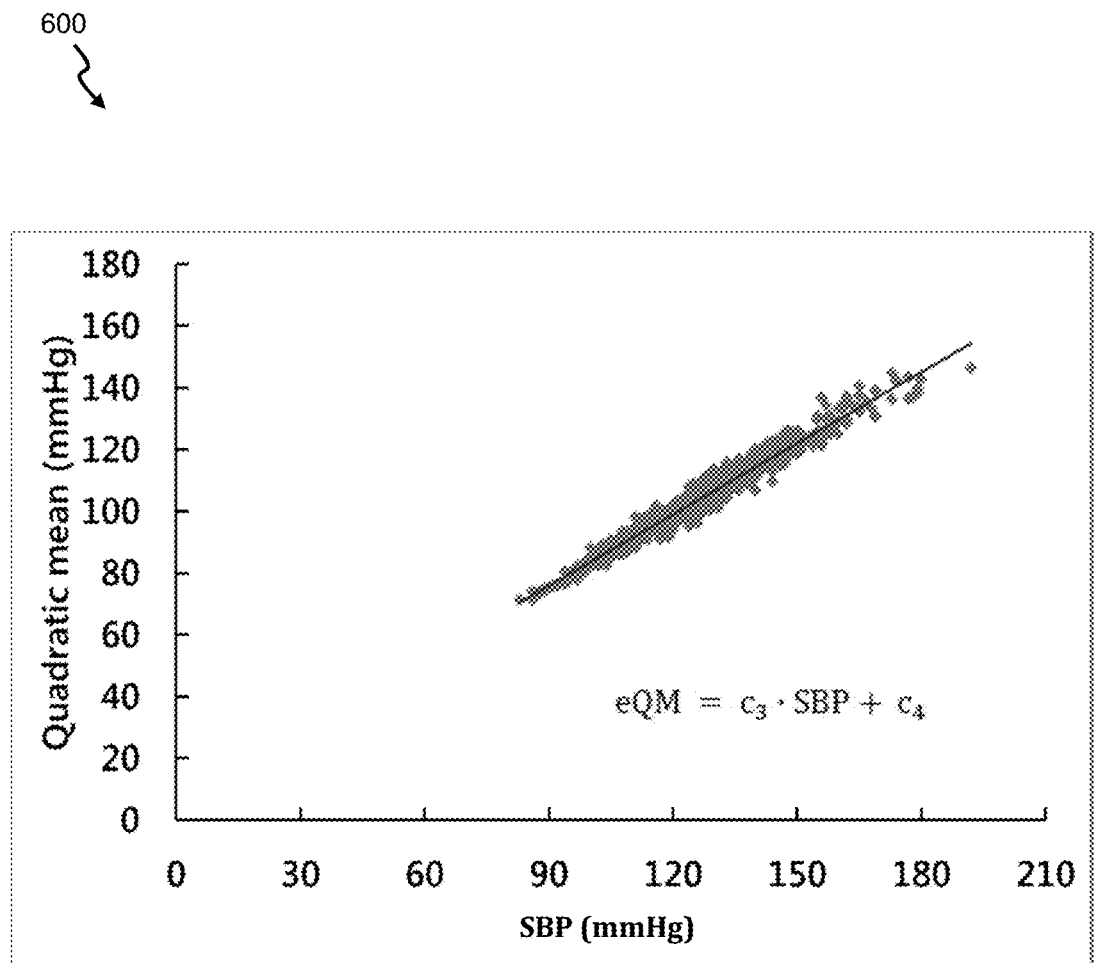
FIG. 6 is a diagram depicting the correlation between eQM values versus measured systolic blood pressure values.

Then at next step 704, the calculation module 114 is configured to calculate an estimated quadratic mean (eQM) based on equation (5), in which FIG. 6 depicts a diagram 600 about the correlation between eQM values versus measured systolic blood pressure values:

$$eQM = c_4 \times SBP + c_5 \quad (5)$$

in which eQM is an estimated quadratic mean; SBP is the systolic blood pressure; and $c_4$, and $c_5$ are predetermined constants. In this instance, the SBP value used in equation (5) is based on the same calculated in equation (4).

In last step 706, the calculation module 124 is arranged to compute a diastolic blood pressure (DBP) of the subject 102, using the SBP and eQM values respectively obtained from equations (4) and (5) above, according to equation (6):

$$DBP = \sqrt{2 \times eQM^2 - SBP^2} + c_6 \quad (6)$$

in which DBP is the diastolic blood pressure; eQM is an estimated quadratic mean; SBP is the systolic blood pressure; and $c_6$ is a predetermined constant.

Figure 8:
FIG. 8 is a table comparing measurement results obtained using the apparatus of FIG. 1 versus results obtained using a conventional blood pressure monitoring device.
Figure 9:
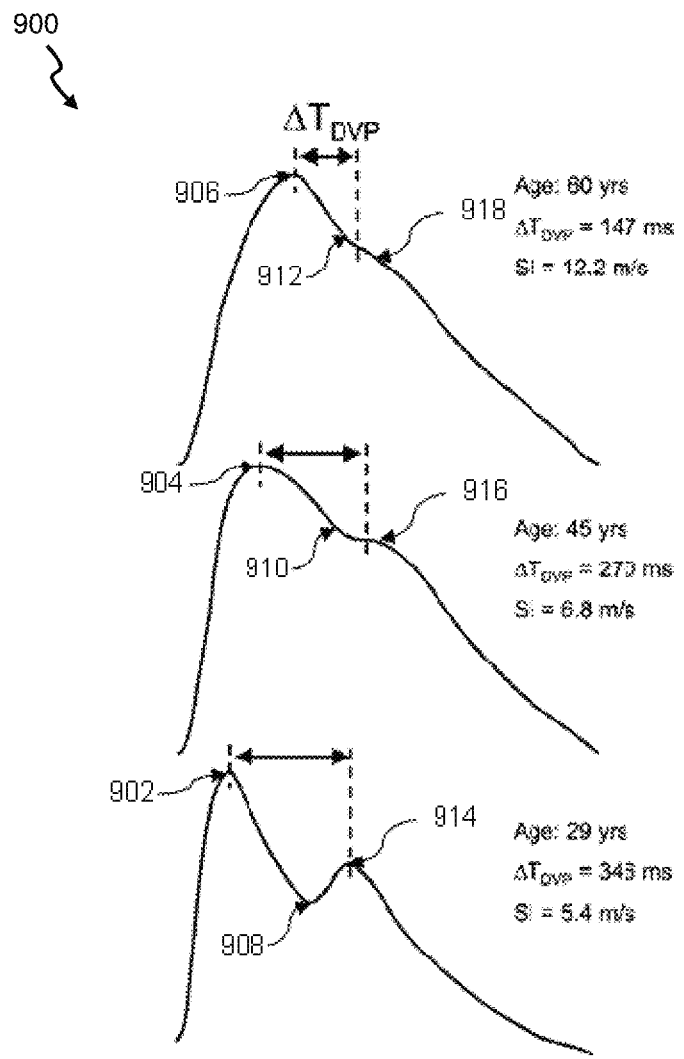
FIG. 9 is a diagram of an arterial waveform, in which effect of age on the diastolic peak and dicrotic notch of the arterial waveform is shown, according to the prior art.

FIG. 8 is a table 800 comparing measurement results obtained using the apparatus 100 of FIG. 1 versus results obtained using a reference conventional blood pressure monitoring device arranged with an arm cuff, such as Omron HEM-7203.

The remaining configurations will be described hereinafter. For the sake of brevity, description of like elements, functionalities and operations that are common between the different configurations are not repeated; reference will instead be made to similar parts of the relevant configuration(s).

In a second embodiment, instead of comprising two separate devices, i.e. the optical measurement device 110 and telecommunication device 120, or the apparatus 100 itself may be implemented as a single equivalent electronic device, in which the optical measurement device 110 and telecommunication device 120 are (hardware) integrated and configured to perform all the same functions described in the first embodiment. Further, all the steps 202-210 of the method 200 (in FIG. 2) may be implemented as a computer program product downloadable over the internet for storing on a memory of the said single electronic device. So, if there are improvements to the method 200 in future, the electronic device may also be updated (as and when required) with those improvements by way of the downloadable computer program product.

In a third embodiment, all the steps 202-210 of the method 200 are performed by one electronic device which may be the telecommunications device 120 or the optical measurement device 110 (which may also be equipped with a display unit). In other words, it is envisaged that the various modules—signal sensing, data processing and calculation modules 112, 114, 124 may form parts of the same electronic device, possibly as part of the optical measurement device 110 or the telecommunications device 120. The single electronic device may also be realised as a wearable sensing device to be worn on the subject's body.

In a fourth embodiment, step 210 of the method 200 may be performed by the data processing module 114 of the optical measurement device 110, instead of the calculation module 124 of the telecommunications device 120, if it is determined that the data processing module 114 (for example) has a higher processing power than the calculation module 124, but is however not to be construed as a sole limiting criterion for the data processing module 114 to execute step 210. Also, performance of step 210 may also dynamically be allocated to the data processing module 114 or calculation module 124, based on a desired arrangement configured by a user of the apparatus 100.

In summary, the proposed method 200 of FIG. 2 (and related apparatus 100) advantageously enables an accurate blood pressure value (i.e. the systolic blood pressure and/or diastolic blood pressure) to be measured (from a single measurement site of the subject 102) using a single optical sensor device, without needing an inflatable cuff, and further without requiring identification of the dicrotic notch and the diastolic peak of an arterial waveform for analysis. Specifically, the proposed method 200 broadly includes the following steps of receiving data related to at least one cardiac cycle of a bio-signal from the subject 102; calculating a rise time and a fall time of the at least one cardiac cycle based on the received data; calculating a parameter derived from a function of the rise time and fall time; and determining the systolic blood pressure and/or diastolic blood pressure of the subject 102 based on the calculated parameter. So, by detecting blood volume changes in the arteries of the subject 102 through PPG techniques, and utilizing various important graphical features of the PPG signal waveform, blood pressure information, i.e. the systolic and diastolic blood pressures, may be calculated from the above disclosed equations (4)-(6).

While the invention has been illustrated and described in detail in the drawings and foregoing description, such illustration and description are to be considered illustrative or exemplary, and not restrictive; the invention is not limited to the disclosed embodiments. Other variations to the disclosed embodiments can be understood and effected by those skilled in the art in practising the claimed invention.

For example, in step 208 of the method 200, if the filtered PPG signal 400 includes a plurality of filtered cardiac cycles, then a corresponding first valley position, a start point 404, a peak position, a systolic peak 406 and a second valley position of each filtered cardiac cycle are to be detected. Further, the SBP value used in equations (5) and (6) need not always be based on the SBP value computed in equation (4). Indeed, the SBP value used in equations (5) and (6) may instead be obtained using suitable conventional methods/apparatuses, independent of the value derived from equation (4). Then, the respective SBP values obtained using the conventional methods/apparatuses, and equation (4) are compared to determine which SBP value actually provides a more accurate result, and consequently, the more accurate SBP value is substituted into equations (5) and (6) for calculating values of the eQM and DBP. Then alternatively, with reference to step 208, the systolic peak 406, start time (i.e. based on the start point 404) and end time (i.e. based on the end point 408) may instead be determined by the data processing module 114 (instead of the calculation module 124), and subsequently, the determined systolic peak 406, start time and end time are transmitted to the calculation module 124 for calculating the rise time and fall time.

It is also to be appreciated that for the condition $-3 \leq x$, $y \leq 3$, where x and y are not equal to zero, the predetermined constants, $c_1$ to $c_6$ (listed in afore disclosed equations (4)-(6)), have the following respective ranges: $-4.11 \leq c_1 \leq 22.18$, $38 \leq c_2 + c_3 \leq 220$, $0.7082 \leq c_4 \leq 0.8170$, $-5.22 \leq c_5 \leq 21.71$, and $-27 \leq c_6 \leq 27$.

Figure 10:
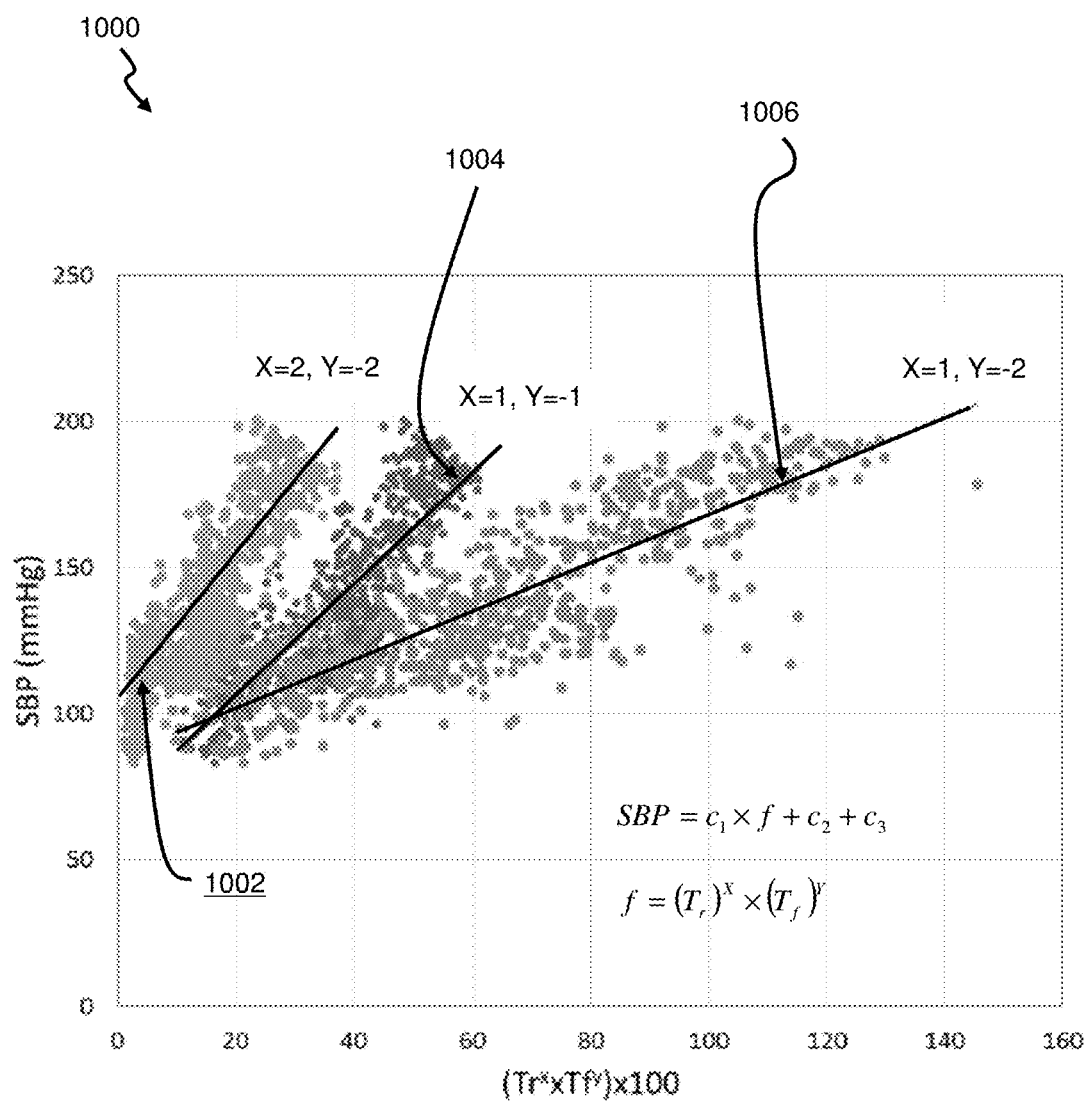
FIG. 10 is a diagram depicting the correlation between systolic blood pressure values and a function of the rise time and fall time.

For good order, FIG. 10 is a diagram 1000 showing the correlation between systolic blood pressure values and a function of the rise time and fall time for the following three sets of conditions: (i). x=2, y=−2 (i.e. see line denoted by reference numeral 1002), (ii). x=1, y=−1 (i.e. see line denoted by reference numeral 1004), and (iii). x=1, y=−2 (i.e. see line denoted by reference numeral 1006).

The invention claimed is:

1. A method of deriving systolic blood pressure and/or diastolic blood pressure of a subject, the method comprising:
(i) measuring, by a single cuffless portable optical measurement device, one or more bio-signals including at least one cardiac cycle;

(ii) calculating, by one or more processors based on the measured one or more bio-signals, a rise time and a fall time of the at least one cardiac cycle;

(iii) calculating, by the one or more processors, a parameter according to the equation:

$$f=(T_r)^X \times (T_f)^Y,$$

where $f$ is the parameter, $T_r$ is the rise time, $T_f$ is the fall time, and x and y are predetermined constants selected from a range of between −3 to 3, and exclusive of 0;

(iv) determining, by the one or more processors based on the calculated parameter, at least one of the systolic blood pressure or the diastolic blood pressure of the subject; and (v) outputting, by a display, the determined at least one of the systolic blood pressure or the diastolic blood pressure.

2. The method of claim 1, wherein the rise time is calculated between a start of the at least one cardiac cycle to a systolic peak of the at least one cardiac cycle.

3. The method of claim 2, wherein the fall time is calculated from the systolic peak of the at least one cardiac cycle to an end of the at least one cardiac cycle.

4. The method of claim 1, wherein the rise time is calculated between 10% and 90% of a systolic peak of the at least one cardiac cycle.

5. The method of claim 1, wherein the one or more bio-signals further includes an arterial photoplethysmography (PPG) signal.

6. The method of claim 5, further comprises processing the PPG signal to digitally filter noise signals in the PPG signal.

7. The method of claim 6, wherein digitally filtering the noise signals in the PPG signal includes using a band pass filter configured to only permit signals having a frequency of between 0.5 Hz to 8.0 Hz to pass through the band pass filter.

8. The method of claim 1, wherein the one or more bio-signals relates to a plurality of cardiac cycles, and the method further includes:

calculating the rise time and the fall time of each of the plurality of cardiac cycles;

calculating, based on a function of the rise time and the fall time of each of the plurality of cardiac cycles, parameters; and calculating, based on the respectively calculated parameters as the parameter in step (iii), an average parameter.

9. The method of claim 8, wherein the plurality of cardiac cycles include being arranged consecutively.

10. The method of claim 1, wherein the one or more bio-signals includes time intervals of the at least one cardiac cycle relating to a systolic peak, start time and end time of the at least one cardiac cycle.

11. The method of claim 1, further comprises determining a systolic peak, a start time and an end time by a first electronic device and transmitting, by the one or more processors, the determined systolic peak, start time and end time to a second electronic device for calculating the rise time and fall time.

12. The method of claim 1, wherein determining the systolic blood pressure includes determining the systolic blood pressure according to the equation:

$$SBP = c_1 \times f + c_2 + c_3,$$

where SBP is the systolic blood pressure;
$f$ is the parameter; and
$c_1$, $c_2$, and $c_3$ are predetermined constants.

13. The method of claim 1, wherein determining the diastolic blood pressure includes determining the diastolic blood pressure according to the equation:

$$DBP = \sqrt{2 \times eQM^2 - SBP^2} + c_6,$$

where DBP is the diastolic blood pressure;
eQM is an estimated quadratic mean;
SBP is the systolic blood pressure; and
$c_6$ is a predetermined constant.

14. The method of claim 13, wherein the estimated quadratic mean is determined according to the equation:

$$eQM = c_4 \times SBP + c_5,$$

where eQM is an estimated quadratic mean;
SBP is the systolic blood pressure; and
$c_4$, and $c_5$ are predetermined constants.

15. A non-transitory computer readable medium storing instructions for deriving systolic blood pressure and/or diastolic blood pressure of a subject, which when executed by one or more processors of a single cuffless portable optical measurement device configured to capture one or more bio-signals cause the one or more processors to:

(i) measure the one or more bio-signals including at least one cardiac cycle;

(ii) calculate, based on the measured one or more bio-signals, a rise time and a fall time of the at least one cardiac cycle;

(iii) calculate a parameter according to the equation:

$$f=(T_r)^X \times (T_f)^Y,$$

where $f$ is the parameter, $T_r$ is the rise time, $T_f$ is the fall time, and x and y are predetermined constants selected from a range of between −3 to 3, and exclusive of 0;

(iv) determine, based on the calculated parameter, at least one of the systolic blood pressure or diastolic blood pressure; and (v) output to a display the determined at least one of the systolic blood pressure or the diastolic blood pressure.

16. A single cuffless optical measurement device for deriving systolic blood pressure and/or diastolic blood pressure of a subject, the single cuffless optical measurement device comprising:

(i) a sensor configured to capture one or more bio-signals including at least one cardiac cycle;

(ii) a display; and (iii) a processor configured to:

(a) measure the one or more bio-signals;

(b) calculate, based on the measured bio-signals, a rise time and a fall time of the at least one cardiac cycle;

(c) calculate a parameter according to the equation:

$$f=(T_r)^X \times (T_f)^Y,$$

where $f$ is the parameter, $T_r$ is the rise time, $T_f$ is the fall time, and x and y are predetermined constants selected from a range of between −3 to 3, and exclusive of 0;

(d) determine, based on the calculated parameter, at least one of the systolic blood pressure or the diastolic blood pressure; and (e) output, to the display, the determined at least one of the systolic blood pressure or the diastolic blood pressure.

* * * * *